United States Patent [19]
Roberts, II et al.

[11] Patent Number: 5,945,295
[45] Date of Patent: *Aug. 31, 1999

[54] METHOD AND COMPOSITIONS TO DETECT AUTOOXIDATION OF LIPIDS OR FATS EX VIVO

[75] Inventors: L. Jackson Roberts, II; Jason D. Morrow, both of Nashville, Tenn.; Eric H. Kuhrts, Woodside, Calif.

[73] Assignees: Vanderbilt University, Nashville, Tenn.; Lipoprotein Diagnostics, Inc., Redwood City, Calif.

[ * ] Notice: This patent is subject to a terminal disclaimer.

[21] Appl. No.: 08/995,480

[22] Filed: Dec. 22, 1997

Related U.S. Application Data

[63] Continuation-in-part of application No. 08/304,147, Sep. 12, 1994, Pat. No. 5,700,654, which is a continuation-in-part of application No. 07/715,419, Jun. 14, 1991, abandoned.

[51] Int. Cl.$^6$ ............ G01N 33/03; C12Q 1/26; C07C 61/06
[52] U.S. Cl. ............ 435/7.92; 435/25; 435/63; 436/71; 436/74; 562/503
[58] Field of Search ............ 435/7.92, 25, 63; 436/71, 74; 562/503

[56] References Cited

U.S. PATENT DOCUMENTS 5,700,654  12/1997  Roberts et al. ............ 435/25

*Primary Examiner*—Cecilia J. Tsang
*Assistant Examiner*—Abdel A. Mohamed
*Attorney, Agent, or Firm*—Kohn & Associates

[57] ABSTRACT

This invention relates to a method to assess food spoilage ex vivo by quantification of prostanoid compounds and their metabolites produced by a noncyclooxygenase free radical catalyzed mechanism.

9 Claims, 4 Drawing Sheets

Fig. 3A  HYDROXYLS
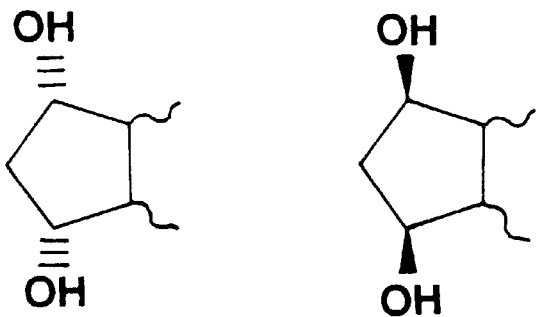
Fig. 3B  SIDE CHAINS
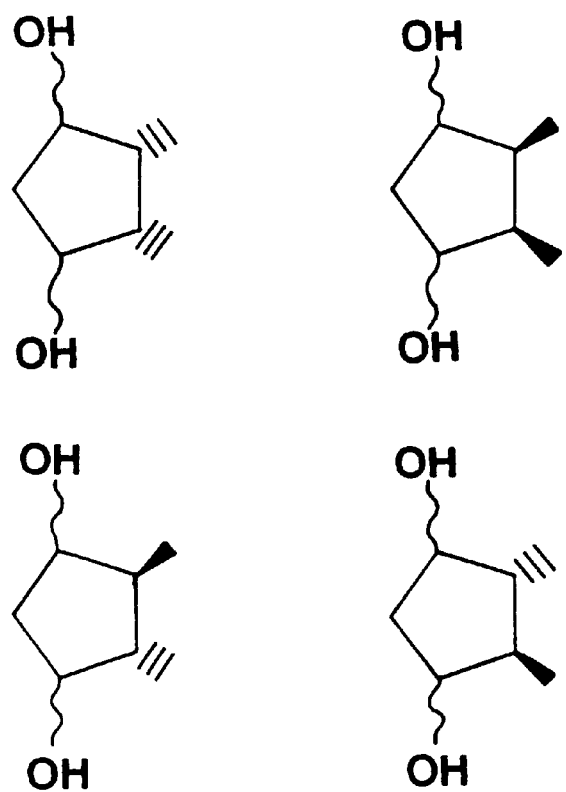

METHOD AND COMPOSITIONS TO DETECT AUTOOXIDATION OF LIPIDS OR FATS EX VIVO

CROSSREFERENCE TO RELATED APPLICATIONS

This application is a continuation-in-part of U.S. Ser. No. 08/304,147 filed Sep. 12, 1994, now U.S. Pat. No. 5,700,654 which is a continuation in part of 07/715,419 filed Jun. 14, 1991, abandoned.

GRANT REFERENCE

Not applicable.

BACKGROUND OF THE INVENTION

1. Field of the Invention

This invention relates to a method to assess oxidation of lipids and fats ex vivo by quantification of prostaglandin-like compounds and their metabolites produced by a non-cyclooxygenase free radical catalyzed mechanism.

2. Description of Related Art

Free radicals derived primarily from oxygen have been implicated in the pathophysiology of a number of human diseases, such as atherosclerosis, ischemia-reperfusion injury, inflammatory diseases, cancer and aging. A variety of methods have been developed to assess oxidative stress and more generally, oxidation or autooxidation of lipids and fats ex vivo i.e. food spoilage; however, some of these methods have limited sensitivity or specificity, while others are either too invasive or not adaptable for human investigation. (Halliwell, et al, 1987)

Free radicals are generally short lived and thus, indirect methods of detection are required (see Pryor, W., 1989) Standard detection methods include: electron spin resonance (directly), electron spin resonance (spin trapping), thiobarbituric acid reactive substances (TBARS), detection of malonaldehyde by direct methods (such as HPLC of malonaldehyde itself or as its dinitrophenylhydrazone), detection of other oxidation products from polyunsaturated fatty acids (such as 4-hydroxynonenal), measurement of lipid hydroperoxides, detection of volatile hydrocarbons (ethane, pentane and ethylene), detection of oxidation products from lipids other than polyunsaturated fatty acids (e.g., cholesterol), oxidation of methional, methionine, or 2-keto-4-thiomethylbutanoic acid to ethylene, oxidation of benzoic acid to carbon dioxide (often with radiolabelled carbon dioxide), oxidation of phenol, benzoic acid, or aspirin to hydroxylated products, determination of decreases in antioxidant levels (e.g., decreased GSH, tocopherol, or ascorbate) or of increases in the oxidized products from antioxidants (e.g., tocopherol quinone or the ascorbyl radical), detection of oxidized DNA bases (e.g., thymine glycol, 8-hydroxydeoxyguanosine), detection of oxidized products from proteins (e.g., methionine sulfoxide from methionine) or of proteins oxidized to carbonyl-containing products that then react with hydride-reducing agents, detection of adducts of DNA bases (e.g., by enzymatic hydrolysis post-labeling using P32), and chemiluminescence methods. (Pryor, 1989).

Unfortunately, oxidative stress is difficult to assess in humans due to lack of reliable methods to assess oxidant stress in vivo. There is also no marketed assessment for food spoilage. As one author stated, "one of the greatest needs in the field now is the availability of non-invasive test to probe the oxidative stress status of humans." (Pryor, 1989)

Morrow, et al. (1990) discovered that a series of prostaglandin $F_2$ -isprostanes, were generated in human plasma during storage at $-20°$ C. for several months or in plasma that had been repeatedly frozen and thawed. Morrow et al. (1990) determined that these compounds were formed by a non-cyclooxygenase mechanism by autooxidation of arachidonic acid contained in plasma. This article demonstrated that prostaglandins could be generated by autooxidation during storage of biological samples which could result in artifactual results with measurements of prostaglandins in stored samples. At that time, there was nothing to suggest that this was anything more than just a non-enzymatic in vitro artifact or phenomenon that occurred during the storage of plasma or other lipid containing biological fluids. In fact, this process, autooxidation of lipids or fats, is a major process responsible for spoilage of food during storage.

SUMMARY OF THE INVENTION AND ADVANTAGES

This invention is based on the discovery that prostanoids, as for example $F_2$- and $F_3$-like compounds, are produced ex vivo by a noncyolooxygenase free radical catalyzed mechanism. More specifically, it has been found that the quantity of free prostaglandin $F_2$-like compounds in food such as meat, poultry and fish, increases in response to agents that cause free radical induced lipid peroxidation and $F_3$-like also.

These prostaglandin $F_2$-like compounds are isomeric to prostaglandins produced by the cyclooxygenase enzyme and are now referred to as $F_2$-isoprostanes. The prostaglandin $F_2$-like compounds produced in response to said free radical induced lipid peroxidation having the following basic structures. Each of the four structures shown are comprised of eight racemic diastereomers:

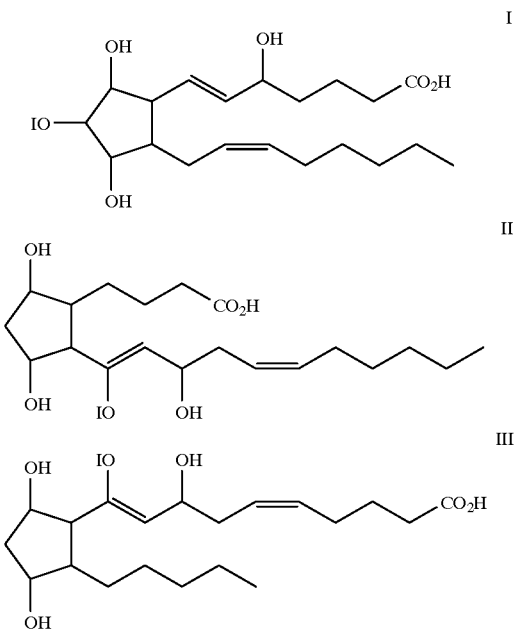

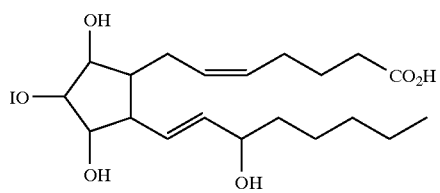

Another embodiment of this invention involves the discovery that the levels of metabolites of prostaglandin $F_2$-like compounds also increase in response to food spoilage. The metabolites of prostaglandin $F_2$-like compounds produced in response to said free radical catalyzed mechanism have the following formula:

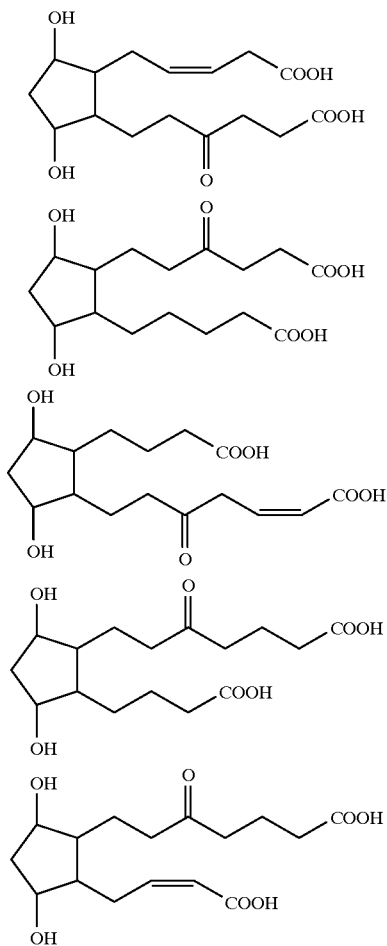

Based on these discoveries, this invention can be used to provide a reliable method to assess food spoilage ex vivo by quantifying prostaglandin $F_2$-like compounds and their metabolites. In particular, this invention provides a method to assess food spoilage ex vivo by obtaining a sample of the food, measuring the amount of noncyclooxygenase derived prostanoid compounds in the sample, comparing the measured amounts of the prostanoids with a control and assessing the spoilage based upon said comparison.

It is an object of this invention to quantify these prostanoid compounds in various foods including: meat, fish, vegetables, milk, juices, oils, cereals, grains and poultry. If the sample contains lipids, the measurement of noncyclooxygenase derived prostanoid compounds should be made prior to the further ex vivo formation of prostaglandin $F_2$-like compounds.

Additionally, this invention provides a method to assess food spoilage ex vivo by measuring the amount of noncyclooxygenase derived metabolites of prostanoids in a sample, comparing the measured amounts of the metabolites of prostanoids with a control and assessing the ex vivo spoilage.

BRIEF DESCRIPTION OF THE DRAWINGS

Other advantages of the present invention will be readily appreciated as the same becomes better understood by reference to the following detailed description when considered in connection with the accompanying drawings wherein:

FIGS. 3A and 3B show possibilities of stereochemical changes of hydroxyls and side chains of the metabolites shown in FIG. 2.

DETAILED DESCRIPTION OF THE INVENTION

The present invention is a method to assess food spoilage ex vivo. The method includes the steps of (a) obtaining a fresh sample of lipid containing food stuff; (b) measuring the amount of noncyclooxygenase derived prostanoids in the sample prior to the further ex vivo development of prostanoids in the sample; and (c) comparing said measured amount of prostanoids with a control. The amount of food spoilage ex vivo is assessed based on the comparison in step (c).

Prostaglandin $F_2$-like compounds are produced in vivo by a noncyclooxygenase free radical catalyzed mechanism. Free prostaglandin $F_2$-like compounds have been quantitated in plasma and urine. The level of individual prostaglandin $F_2$-like compounds in plasma ranges from approximately 5-50 picograms/mL and in urine from approximately 500–3000 picogramns/miL.

Figure 1:
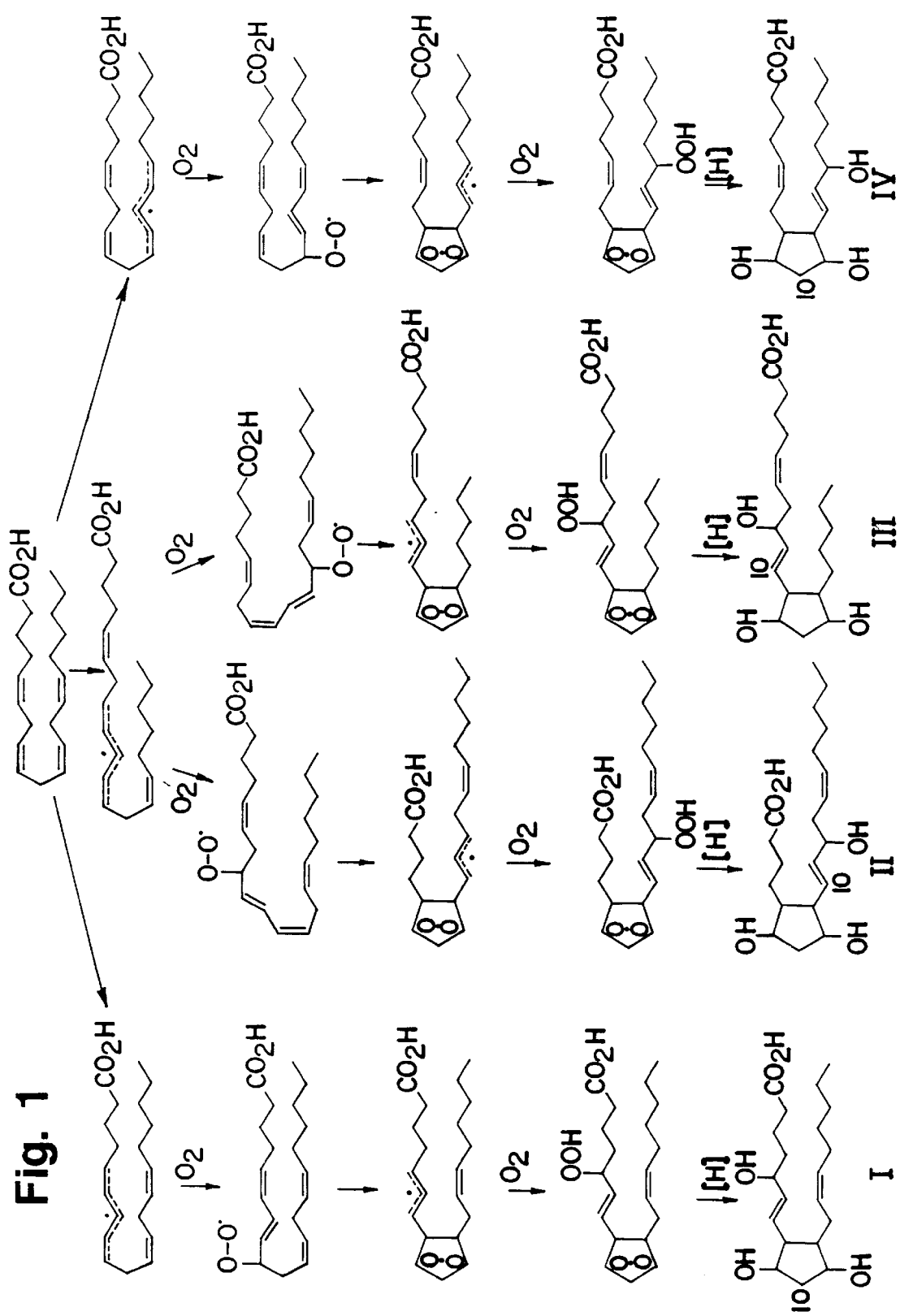
FIG. 1 shows noncyclooxygenase free radical catalyzed mechanism for the formation of prostaglandin $F_2$-like compounds and the chemical structure of four regioisomers.
Figure 2:
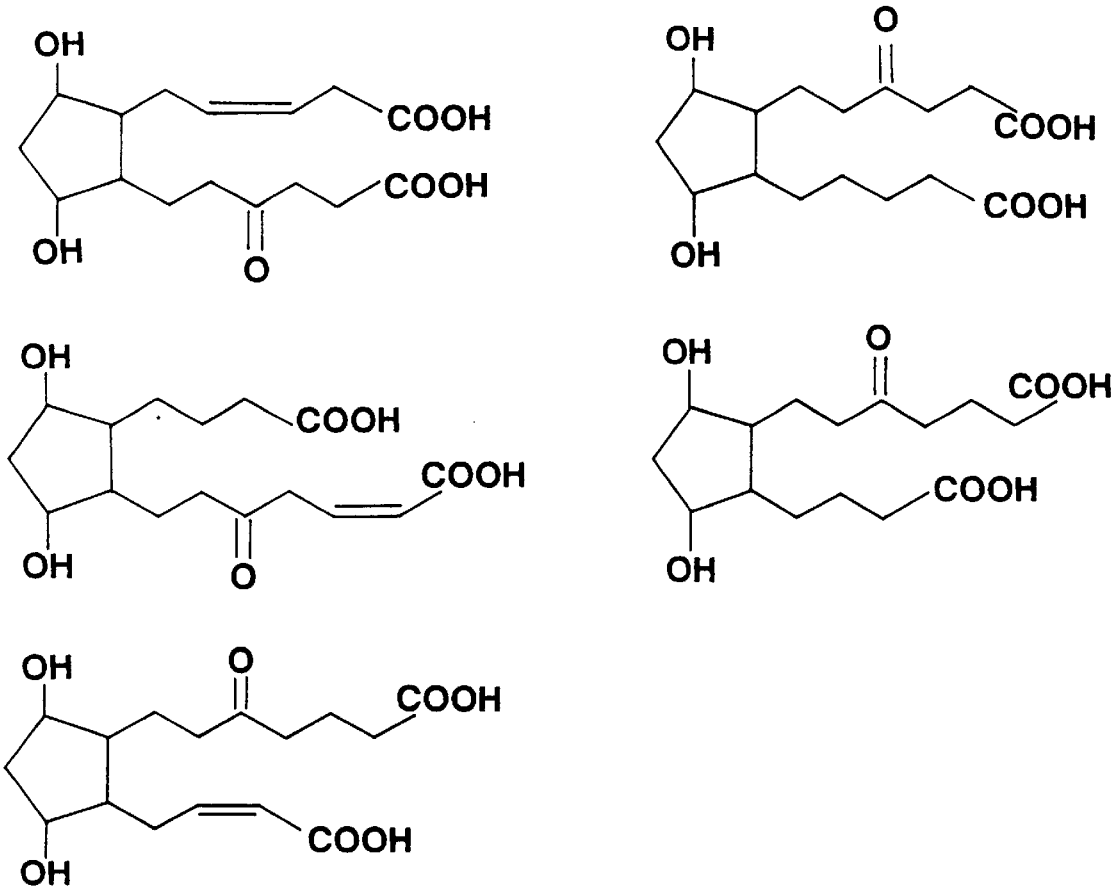
FIG. 2 shows the chemical structure of noncyclooxygenase derived prostaglandin $F_2$-like urinary metabolites.

The prostaglandin $F_2$-like compounds are produced in vivo and ex vivo by free radical catalyzed mechanism. In particular, electron ionization mass spectra analysis of human urine shows four prostaglandin $F_2$-like regioisomers. FIG. 1.

The quantity of free pro staglandin $F_2$-like compounds in food, such as meats, fish and poultry, increases in response to agents that cause free radical induced lipid peroxidation. Circulating levels of the compounds were shown to increase by as much as 200-fold in animal models of free radical induced lipid peroxidation. The herbicide diquat undergoes redox cycling in vivo leading to the production of superoxide anions. When diquat is administered to Se-deficient rats, marked lipid peroxidation ensues. Circulating levels of prostaglandin $F_2$-like compounds in plasma obtained 1½ hours following administration of diquat to eight Se-deficient rats were dramatically elevated from 27 to 200-fold above levels measured in Se-deficient control rats that did not receive diquat. The pattern of the elevated prostaglandin $F_2$-like compounds in treated rats also was essentially identical to the pattern seen in untreated rats.

$F_3$-like isoprostanes have been found in fish oil (Nour00z-Zadeh, et al. 1997) formed following non-enzymatic peroxidation of orschidonic acid. Specifically, 8-Ep:PGF3 alpha was measured. Formation of $F_3$-isoprostanes correlated well with other indices of lipid peroxidation.

The second animal model employed administration of carbon tetrachloride to normal rats. This leads to the formation of $CCl_3$ radicals which catalyze lipid peroxidation. Treatment of six rats with carbon tetrachloride also resulted in marked increases in the circulating levels of prostaglandin $F_2$-like compounds ranging from 10 to 30-fold above normal. In addition, pretreatment of the rats with high doses of indomethacin to inhibit cyclooxygenase activity failed to suppress the production of these compounds following administration of carbon tetrachloride.

Collectively, the above results have established that there are a unique class of prostanoids that are produced in vivo and ex vivo by a noncyclooxygenase mechanism involving free radical catalyzed lipid peroxidation.

It should be understood that it is possible that prostaglandin $D_2$-like and prostaglandin $E_2$-like compounds may form from isomerization of prostaglandin $G_2$-like endoperoxide intermediates in aqueous solutions. Incubation of human plasma ex vivo yields significant amounts of prostaglandin $D_2$-like and prostaglandin $E_2$-like compounds when analyzed by gas chromatography selected ion monitoring negative ion chemical ionization mass spectrometry. The inventors have obtained evidence that noncyclooxygenase derived prostaglandin $D_2$-like and E2-like compounds are present acylated to liver phospholipids in vivo.

Since the quantity of free prostaglandin $F_2$-like compounds in human plasma or urine as well as food stuffs increases in response to agents that cause free radical induced lipid peroxidation, an assay to measure oxidative stress in vivo and food spoilage ex vivo has been devised. Prostaglandin $F_2$-like compounds facilitate this analysis because they are easily detected in normal human biological fluids.

One drawback discovered relating to the use of these free prostaglandin $F_2$-like compounds as a means to assess oxidative stress is the ex vivo generation of prostaglandin $F_2$-like compounds in certain biological fluids. Arachidonyl containing lipids in plasma readily undergo peroxidation in vitro leading to the formation of these prostanoids. The inventors have found that plasma can be allowed to stand at room temperature for up to two hours without levels of these compounds increasing significantly. However, these compounds can be generated in substantial quantities if plasma is allowed to stand for longer periods of time, if plasma is frozen and thawed several times, or if plasma is subjected to storage at $-20°$ C. for periods of time such as a few weeks. The problem of artificial generation of these compounds can be minimized, but not totally eliminated, by addition of antioxidants to the sample. Thus, to avoid these potential sources of error, plasma that is obtained for analysis should not be stored and should be processed for analysis within approximately two hours. However, it is not necessary to process the plasma sample completely through the assay.

Plasma phospholipids containing arachidonic acid are the lipid source for which these compounds are generated ex vivo. Although phospholipids are generally retained by C-18 reverse phase chromatography packing, the inventors have found that phospholipids in plasma are not, presumably due to binding to plasma proteins. Thus, when plasma is initially subjected to solid phase extraction using a C-18 cartridge, free prostaglandin $F_2$-like compounds present in the plasma are retained and the phospholipids are quantitatively removed in the initial aqueous phase elute. After the retained prostaglandin $F_2$-like compounds are eluted with a 1:1 mixture of ethyl acetate:heptane, they can be stored at $-20°$ C. and processed later without the problem of ex vivo generation.

The inventors have also recently found that whereas these prostaglandins are generated ex vivo in plasma during storage at $-20°$ C., formation of these compounds did not occur while the plasma was stored for five months at $-70°$ C.

The above discussed problem surrounding plasma undoubtedly applies to any biological fluid or food stuff which contains significant quantities of lipids which can be the source of ex vivo generation of these prostanoids. This problem however is not encountered with analysis of urine. Urine contains very few lipids and the inventors have found that the levels of prostaglandin $F_2$-like compounds do not increase during storage of urine for up to six months at $-20°$ C. or during incubation of urine for seven days at $37°$ C. However, there is a potential problem associated with the quantification of these compounds in urine as an index of their systematic production. At present, the inventors do not know the primary source from which the compounds present in urine are derived. Specifically, it is not known if they originate primarily from plasma via filtration by the kidney or if they arise primarily from local production in the kidney. Urinary cyclooxygenase derived prostaglandins have been shown to arise almost exclusively from local formation in the kidney. If this is also the case with the noncyclooxygenase derived prostanoids, then quantification of these compounds in urine could be used to assess oxidant stress in the kidney but this approach could not be used as an index of their systemic production.

Recently, however, the inventors have obtained data which may provide a new dimension on the ability to assess endogenous production of these compounds which circumvents the above discussed problems. In the process of developing a mass spectrometric assay for the major urinary metabolite of cyclooxygenase derived prostaglandin $D_2$, the inventors have identified urinary metabolites of these noncyclooxygenase derived prostaglandin $F_2$-like compounds in human urine. The metabolites have the same basic atomic composition as the prostoglandin $D_2$ metabolite (9α, 11β-dihydroxy-15-oxo-2, 3, 18, 19-tetranorprostane-1, 20-dioic acid), but are structurally different. See FIGS. 3A & 3B and 4. The levels of metabolites of the noncyclooxygenase derived $F_2$-like compounds are not suppressed by treatment with cyclooxygenase inhibitors. Additionally, it has been found that metabolite levels increase significantly inurine following administration of carbon tetrachloride to rats. The ability to quantify a metabolite of these compounds would be extremely valuable in that it would provide an index of systemic production of these compounds without the inherent potential problems of artifactual generation of the compound ex vivo.

Still another alternative embodiment involves a discovery that tissue and food stuff samples could also be analyzed for prostaglandin $F_2$-, $D_2$-, $F_3$- and $E_2$-like compounds. This observation was unexpected and surprising. Arachidonic acid is the precursor of both enzymatically derived prostaglandins and the prostaglandin $F_2$-like compounds formed by non-enzymatic peroxidation of arachidonic acid. Arachidonic acid is almost entirely stored esterified to tissue phospholipids, with only small amounts being present in free form in cells.

During enzymatic formation of prostaglandins, arachdonic acid has to be released from phospholipids by phospholipases to be metabolized by the cyclooxygenase enzyme to form prostaglandins. Once the enzymatically formed prostaglandins are produced, they are released from cells and not stored and are not found esterified to phospholipids in tissues. Thus, tissue levels of prostaglandins are essentially unmeasurable.

When phospholipids are subjected to oxidation, it is known that fatty acid hydroperoxides have been shown to be readily cleaved from phospholipids by phospholipases. One question the inventor investigated was whether, in contrast to cyclooxygenase derived prostaglandins, the prostaglandin $F_2$-like compounds are formed intact on phospholipids during free radical catalyzed peroxidation of lipids or whether only the oxidized precursors, i.e. the fatty acid hydroperoxides, are formed on phospholipids which are then cleaved by phospholipases and subsequently undergo the further transformation to yield prostaglandin $F_2$-like compounds. Experiments were carried out which provided direct evidence that the prostaglandin $F_2$-, $D_2$-, $F_3$- and $E_2$- and $E_2$-like compounds are actually formed in situ esterified to phospholipids and that the levels of the compounds esterified to phospholipids in tissues of the rat following administration of $CCl_4$ to induce lipid peroxidation increased dramatically compared to levels in tissues of untreated rats.

These findings suggest another approach to assess oxidant status in tissues and food stuffs in some human disorders. The sensitivity of the method of detection allows the inventors to detect prostaglandin $F_2$-like containing phospholipids in very small pieces of tissue well within the amount of tissue that would ordinarily be obtained in a routine biopsy. Biopsies of a variety of tissues are routinely obtained for the diagnosis of numerous types of human diseases. For example, a number of liver diseases including alcohol liver damage are speculated to involve free radical induced injury. One problem that we have recognized with measuring levels of free compounds in plasma or urine or their metabolites is that local formation of these compounds at a limited site in the body may not be associated with the release of free compounds in quantities sufficient to significantly elevate the basal levels that we see in plasma or urine in normal humans. In these situations it may require sampling of blood draining directly from the site of suspected pathophysiology. This can be very impractical and/or impossible in many situations in humans. However, if a biopsy is obtained of an involved tissue or organ, this approach may allow us to directly assess oxidant status in the biopsy tissue by measuring the level of prostaglandin $F_2$-like compounds esterified to tissue phospholipids. This approach could therefore be used to directly obtain evidence for the occurrence of free radical induced injury in the pathophysiology of a wide variety of human diseases.

One possible method to detect the quantity of prostaglandin such as $F_2$-like and $F_3$-like compounds in biological fluids and food stuffs is mass spectroscopy. This type of assay for prostaglandin compounds or their metabolites offers several advantages: First, the mass spectrometric assay is very sensitive with a lower limit of detection in the range of 1 picogram. Second, the assay has a high degree of specificity and accuracy.

The present method is a stable isotope dilution assay employing capillary gas chromatography negative ion chemical ionization mass spectrometry. In an embodiment heptadeuterated 9α, 11β-prostaglandin $F_2$ or deuterated prostaglandin $F_2α$ is used as the internal standard. Prostaglandin $F_2$-like compounds are extracted by solid phase techniques using a C-18 cartridge and subsequently purified by thin layer chromatography. Analysis by mass spectrometry is accomplished as a pentaflurobenzyl ester, trimethylsilyl ether derivative. Quantification is performed by selected ion monitoring of the ratio of the M-181 (loss of $°CH_2C_6F_6$) ions at m/z 569 for endogenous prostaglandin $F_2$-like compounds and m/z 576 for the internal standard. The assay has a precision of ±6% and an accuracy of 96%. Lower limits of detection are in the range of approximately 1 picogram. See FIG. 4.

The basic assay can be employed and adapted for measurement of these compounds in a wide variety of biological fluids and food stuffs. In addition to plasma and urine, the assay can be used with cerebrospinal fluid, bile, lung lavage fluid, lymph, and inflammatory human joint fluid. Food stuffs as listed above can likewise be assayed.

In an alternative embodiment, the prostaglandin-like compounds can be assayed using immunoassays. Immunoassay is a suitable method for the detection of small amounts of specific prostanoids (5–500 picograms can be readily detected). In particular, antibodies can be raised to these prostaglandin-like compounds using conventional techniques. The antibodies can then be used in immunoassays to quantitate the amount of prostaglandin-like compounds in the biological fluid.

A small molecule (less than 5–10 kildaltons) will usually not elicit the production of antibodies in experimental animals unless covalently linked to large immunogenic molecules prior to immunization. The noncyclooxygenase derived prostaglandin-like compound, such as, 8-epi-prostaglandin $F_2α$ can be coupled via its carboxyl group to a carrier protein by the dicyclohexyl-carbodiimide method. (Rich, D. H., et al. 1979; U.S. Pat. No. 4,859,613). 8-epi-prostaglandin $F_2α$ can be coupled to keyhole limpet hemocyanin (KLH) by the DCC method used by Levine et al. (1980). Accordingly, 8 mg. Of 8-epi-prostaglandin $F_2α$ are dissolved in 100 μl of N,N-dimethyl formamide. The 8-epi-prostaglandin $F_2α$ is then activated by the addition of 3 mg of DCC in the presence of 3.5mg. of N-hydroxysuccinimide as a trapping agent. This reaction mixture is stirred for 30 minutes at room temperature. As the reaction proceeds the byproduct dicyclourea will form a white precipitate. When the reaction is complete, this precipitate is removed by centrifugation. The supernatant is then added to 6.25 gm of KLH in 0.5 ml of 0.1N $NaHCO_3$ and stirred for two hours at 4° C. the conjugate is then extensively dialyzed against PBS, pH 7.5 (0.15M NaCl, 0.005M $NaHPO_4$). The conjugate is aliquoted and stored at −20° C. It should be noted that many unsaturated fatty acids and their derivatives, are sensitive to oxidation. However, this does not hold for,prostanoids which have only a single double bond on each side chain. Prostaglandin $F_2$-like compounds are extremely stable, can withstand strong base and strong acid and are not susceptible to oxidation. Hence, although there is no facile method by which to determine the integrity of the 8-epi-prostaglandin $F_2α$ haptens attached to KLH, it is unlikely to undergo degradation or modification that could impede the production of specific antisera.

These immunogens can then be used to raise antibodies. Rabbits can be immunized with the 8-epi-prostaglandin $F_2α$-KLH conjugate administered in Complete Freund's Adjuvant. One immunization dosing and scheduling is as follows: 100 µL of conjugate in Complete Freund's Adjuvant will be administered at multiple subcutaneous sites for the primary immunization. At subsequent two week intervals 100 µL of conjugate in Incomplete Freund's Adjuvant will be administered at multiple subcutaneous sites to boost titers. Serum will be collected from animals one week following the initial boost and titers will be determined by ELISA. Similarly, myeloma that secrete monoclanal antibodies can be prepared following the techniques described by Kohler & Milstein (1975).

These antibodies can be used in immunoassays for non-cyclooygenase derived prostaglandin-like compounds. Typical assays for these types of compounds include enzyme-linked immunoassays, fluorescent immunoassays, and radioimmunoassays. The assays can be in the sandwich or competitive formats. See, e.g., David, U.S. Pat. Nos. 4,376,110 and 4,486,530.

Example 1

Figure 4:
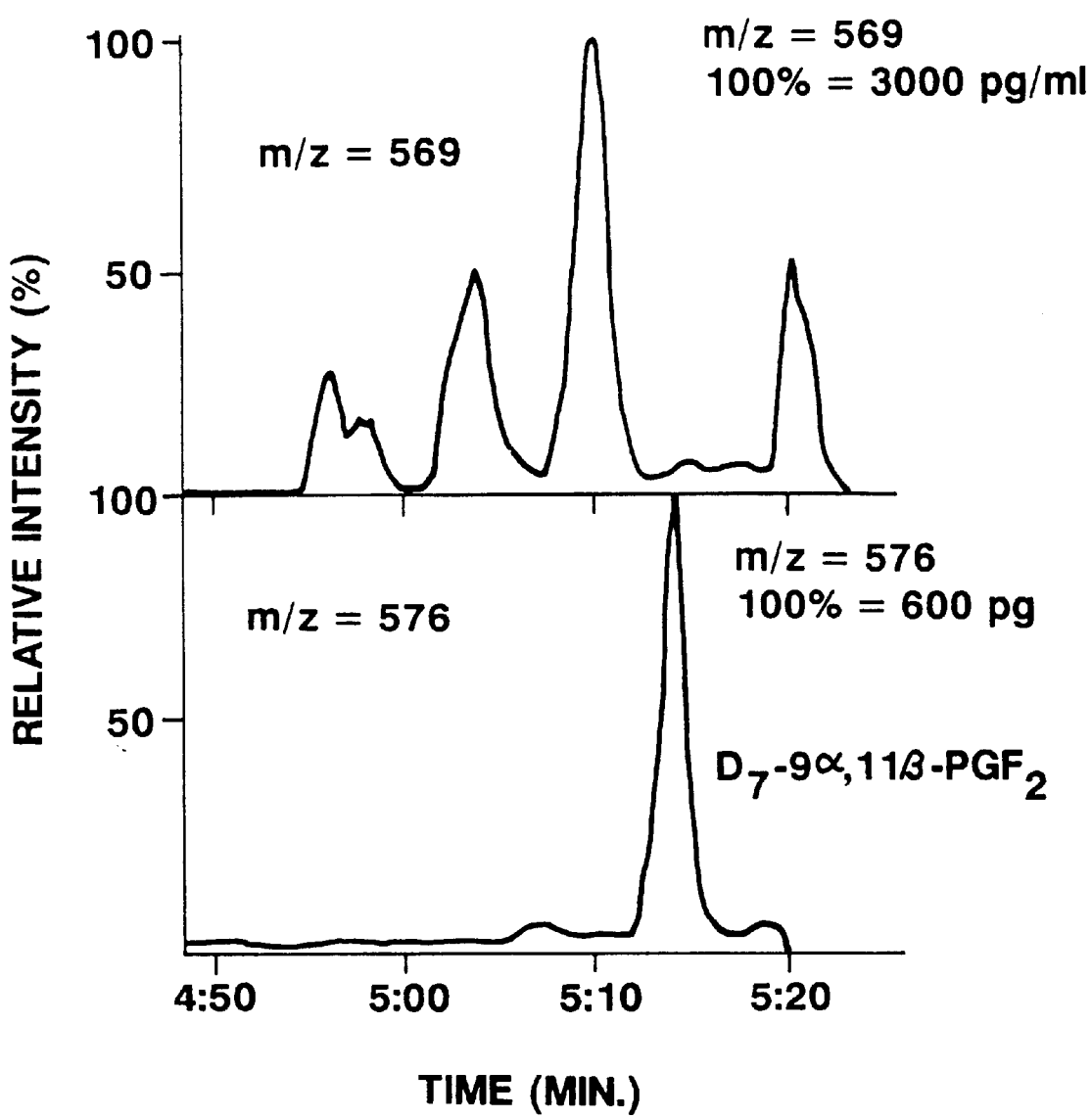
FIG. 4 shows selected ion current chromatogram obtained from the analysis of prostaglandin F2-like compounds in normal human urine. Below is the m/z 576 peak representing the ($^2H_7$) 9α, 11β-prostaglandin $F_2$ internal standard. At the top is the m/z 569 chromatogram which reveals a series of peaks representing endogenous urinary prostaglandin $F_2$-like compounds. Levels of the individual compounds range from approximately 500 to 3000 picograms/mL.

Mass Spectroscopic Assay for Prostaglandin $F_2$-like Compounds in Urine. (FIG. 4).

1 mL of fresh human urine was analyzed in a stable isotope dilution assay for endogenous prostaglandin $F_2$-like compounds. At the bottom of each chromatogram is the m/z 576 peak representing the internal standard. At the top of each tracing are the m/z 569 chromatograms which reveal a series of peaks presumably representing endogenous prostaglandin $F_2$-like compounds. See FIG. 4. The levels of the individual compounds in plasma range from approximately 5–50 picogram/ml. Employing a variety of approaches, including electron ionization mass spectral analysis of these compounds form 1 liter of human urine, it was firmly established that these peaks indeed represented regioisomers of prostaglandin $F_2$-like compounds show in FIG. 1.

Administration of high doses of cyclooxygenase inhibitors to normal volunteers failed to suppress the levels of these compounds measured in fresh normal human plasma and urine, indicating that their formation occurs independent of cyclooxygenase activity. Further studies established that the levels measured in fresh plasma and urine do not arise from ex vivo formation in that the presence of antioxidants in the specimen collecting containers did not suppress the levels measured and levels in urine did not increase during incubation for several days at 37° C. or during storage for up to 6 months at −20° C. In addition, levels were not suppressed by a diet consisting solely of glucose polymers, indicating that these compounds do not arise from dietary sources.

Throughout this application, various publication are referenced by author and year and patents by number. Full citations for the publication are listed below. The disclosure of these publications in their entireties are hereby incorporated by reference into this application in order to more fully describe the state of the art to which this invention pertains.

While the present invention has been described by reference to certain illustrative examples, various modifications and variance within the spirit and scope of the invention will be apparent to those skilled in the art.

Obviously, many modifications and variations of the present invention are possible in light of the above teachings. Therefore, it is to be understood that within the scope of the appended claims, the invention may be practiced otherwise than as specifically described.

REFERENCES CITED

Halliwell, B., et al. The Measurement Of Free Radical Reactions In Humans: Some Thoughts For Future Experimentation. *FEBS Letters*. 213:9–14, 1987.

Levine, et al. 1980, Prostaglandins 20: 923–934.

Morrow et al., "Noncyclooxygenase Oxidative Formation of a Series of Novel Prostaglandins: Analytical Ramifications for Measurement of Eicosanoids", *Anal. Biochem.* 184:1–10(1990).

Nourooz-Zadah, et al., 1997. "Evidence for the formation of F3-isoprostanes during peroxidation of eicosapentaenoic acid", Biochem. Biophys. Res. Comm. 236(2):467–472.

Pryor, W., *On the Detection Of Lipid Hydroneroxides In Biological Samples*, FREE RADICAL BIOLOGY & MEDICINE, Vol. 7, pages 177–178, 1989.

Rich, D. H., et al., The Peptides, 1:241–261 (1979)

What is claimed is:

1. A method to assess food spoilage ex vivo comprising:
   (a) obtaining a fresh sample of lipid containing food stuff;
   (b) measuring the amount of noncyclooxygenase derived prostanoids in the sample prior to the further ex vivo development of prostanoids in the sample;
   (c) comparing said measured amount of prostanoids with a control; and
   (d) assessing food spoilage ex vivo based on the comparison in step (c).

2. The method of claim 1, wherein said food stuff is selected from the group consisting of meat, fish, poultry, juice, fruits, vegetables, oils, cereals, grains and milk.

3. The method of claim 1, wherein said measurement occurs within about two hours of sampling.

4. The method of claim 1, wherein said prostanoids are selected from the group consisting of:

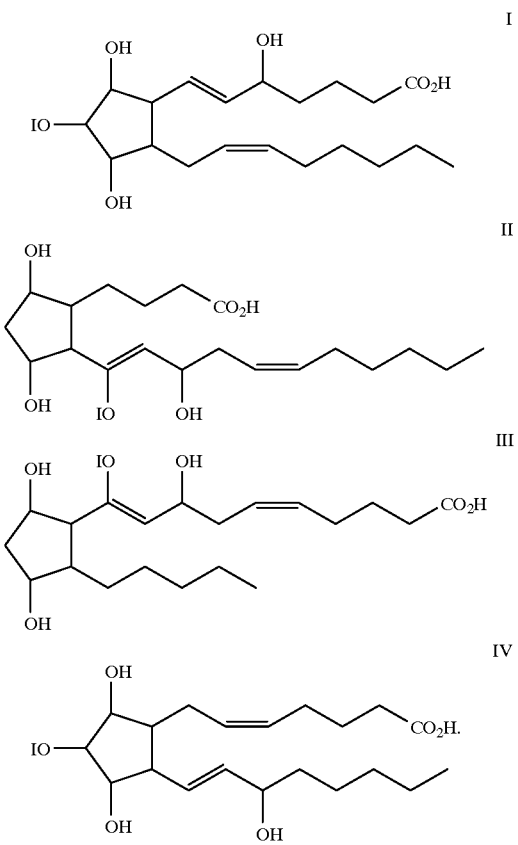

5. The method of claim 1, wherein said prostanoids are prostaglandin $F_2$-like metabolites selected from the group consisting of:

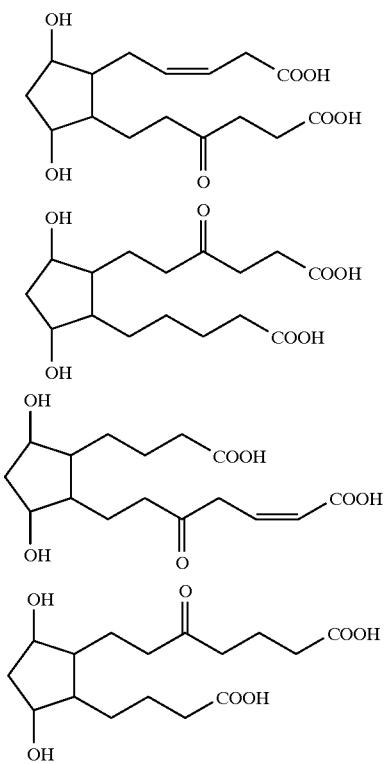

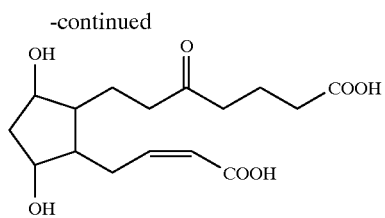

6. The method of claim 1, wherein said prostanoids are prostaglandin $F_3$-like metabolites.

7. A method to assess food spoilage ex vivo comprising;
(a) obtaining a sample of food stuff;
(b) measuring the amount of noncyclooxygenase derived prostaoids in the sample;
(c) comparing said measured amount of prostanoid with a control; and
(d) assessing food spoilage ex vivo based on the comparison in step (c).

8. A method to assess food spoilage ex vivo comprising:
(a) obtaining a sample of food stuff;
(b) measuring the amount of noncyclooxygenase derived prostanoids present in phospholipids in the sample;
(c) comparing said measured amount of said prostanoids with a control; and
(d) assessing the food spoilage based on the comparison in step c.

9. The method of claim 8, wherein said measurement occurs within two hours of sampling.

* * * * *